US010039520B2

(12) United States Patent
Guion-Johnson

(10) Patent No.: US 10,039,520 B2
(45) Date of Patent: Aug. 7, 2018

(54) DETECTION OF CORONARY ARTERY DISEASE USING AN ELECTRONIC STETHOSCOPE

(75) Inventor: Marie A. Guion-Johnson, Farmington, MN (US)

(73) Assignee: AUM CARDIOVASCULAR, INC, Northfield, MN (US)

( * ) Notice: Subject to any disclaimer, the term of this patent is extended or adjusted under 35 U.S.C. 154(b) by 649 days.

(21) Appl. No.: 12/406,849

(22) Filed: Mar. 18, 2009

(65) Prior Publication Data

US 2009/0177107 A1     Jul. 9, 2009

Related U.S. Application Data

(63) Continuation of application No. 11/402,654, filed on Apr. 12, 2006, now Pat. No. 7,520,860.

(Continued)

(51) Int. Cl.
    *A61B 5/02*         (2006.01)
    *A61B 7/04*         (2006.01)

(52) U.S. Cl.
    CPC ..................................... *A61B 7/04* (2013.01)

(58) Field of Classification Search
    CPC ....................................................... A61B 7/04

(Continued)

(56) References Cited

U.S. PATENT DOCUMENTS 3,830,223 A     8/1974   Beretsky et al.
3,951,140 A     4/1976   Eggleton et al.

(Continued)

FOREIGN PATENT DOCUMENTS

EP           2462871       6/2012
WO      WO9905962     2/1999

(Continued)

OTHER PUBLICATIONS

US 9,602,911, 03/2017, Qian (withdrawn)

(Continued)

*Primary Examiner* — Tiffany Weston
*Assistant Examiner* — Tho Tran
(74) *Attorney, Agent, or Firm* — Patterson Thuente Pedersen, P.A.

(57) ABSTRACT

The disclosure describes an electronic stethoscope system that automatically detects coronary artery disease in patients. The system uses an electronic stethoscope to record acoustic data from the fourth left intercostal space of a patient. A processing technique is then applied in order to filter the data and produce Fast Fourier Transform (FFT) data of magnitude versus frequency. If a bell curve is identified in the data between a predefined frequency range (e.g., 50 and 80 Hz) with a peak magnitude of greater than a predefined threshold (e.g., 2.5 units), the system automatically provides an output indicating that the patient is likely to have 50 to 99 percent stenosis of the coronary artery. If no bell curve is present, the patient may have artery stenosis of less than 50 percent. An interface module may be used to transfer diagnosis information to the stethoscope and data to a general purpose computer. This inexpensive and quick system may improve the chances for early detection and patient survival of coronary artery disease.

13 Claims, 8 Drawing Sheets

Related U.S. Application Data

(60) Provisional application No. 60/670,905, filed on Apr. 13, 2005.

(58) Field of Classification Search
USPC .................................................. 600/528, 586
See application file for complete search history.

(56) References Cited

U.S. PATENT DOCUMENTS

| | | | |
|---|---|---|---|
| 4,373,532 A | 2/1983 | Hill et al. | |
| 4,719,923 A | 1/1988 | Hartwell et al. | |
| 4,759,374 A | 7/1988 | Kiemey et al. | |
| 4,905,706 A | 3/1990 | Duff et al. | |
| 4,947,859 A | 8/1990 | Brewer et al. | |
| 5,010,889 A | 4/1991 | Bredesen et al. | |
| 5,035,247 A | 7/1991 | Heimann | |
| 5,036,857 A | 8/1991 | Semmlow et al. | |
| 5,109,863 A | 5/1992 | Semmlow et al. | |
| 5,159,932 A | 11/1992 | Zanetti et al. | |
| 5,218,969 A | 6/1993 | Bredesen et al. | |
| 5,337,752 A | 8/1994 | Reeves | |
| 5,365,937 A | 11/1994 | Reeves et al. | |
| 5,617,869 A | 4/1997 | Austin et al. | |
| 5,638,823 A | 6/1997 | Akat et al. | |
| 5,685,317 A | 11/1997 | Sjöström | |
| 5,687,738 A | 11/1997 | Shapiro et al. | |
| 5,722,419 A | 3/1998 | Semmlow et al. | |
| 5,807,268 A | 9/1998 | Reeves et al. | |
| 5,825,895 A | 10/1998 | Grasfield et al. | |
| 5,885,222 A | 3/1999 | Kassal | |
| 5,913,826 A | 6/1999 | Blank | |
| 5,913,829 A | 6/1999 | Reeves et al. | |
| 5,957,866 A | 9/1999 | Shapiro et al. | |
| 6,002,777 A | 12/1999 | Grasfield et al. | |
| 6,005,915 A | 12/1999 | Hossain et al. | |
| 6,048,319 A | 4/2000 | Hudgins et al. | |
| 6,050,950 A | 4/2000 | Mohler | |
| 6,053,872 A * | 4/2000 | Mohler .................... | 600/485 |
| 6,134,331 A | 10/2000 | Baekgaard | |
| 6,135,966 A | 10/2000 | Ko | |
| 6,152,879 A | 11/2000 | Mohler | |
| 6,179,783 B1 | 1/2001 | Mohler | |
| 6,193,668 B1 | 2/2001 | Chassaing et al. | |
| 6,243,599 B1 | 6/2001 | Van Horn | |
| 6,261,237 B1 | 7/2001 | Swanson et al. | |
| 6,278,890 B1 | 8/2001 | Chassaing et al. | |
| 6,328,698 B1 * | 12/2001 | Matsumoto ........ | A61B 5/02133 600/481 |
| 6,371,924 B1 | 4/2002 | Stearns | |
| 6,477,406 B1 | 11/2002 | Turcott | |
| 6,478,744 B2 | 11/2002 | Mohler | |
| 6,478,746 B2 | 11/2002 | Chassaing et al. | |
| 6,527,729 B1 | 3/2003 | Turcott | |
| 6,533,736 B1 | 3/2003 | Moore | |
| 6,544,189 B2 | 4/2003 | Watrous | |
| 6,572,560 B1 | 6/2003 | Watrous et al. | |
| 6,574,494 B2 | 6/2003 | Horn | |
| D477,405 S | 7/2003 | Sommerfeld et al. | |
| 6,589,189 B2 | 7/2003 | Meyerson et al. | |
| 6,699,201 B2 | 3/2004 | Stearns | |
| 6,709,399 B1 | 3/2004 | Shen et al. | |
| 6,733,450 B1 | 5/2004 | Alexandrov et al. | |
| 6,780,159 B2 | 8/2004 | Sandler et al. | |
| 6,875,176 B2 | 4/2005 | Mourad et al. | |
| 6,878,117 B1 | 4/2005 | Watrous | |
| 6,898,459 B2 | 5/2005 | Hayek et al. | |
| 6,939,308 B2 | 9/2005 | Chassaing et al. | |
| 6,947,789 B2 | 9/2005 | Selvester et al. | |
| 6,953,436 B2 | 10/2005 | Watrous et al. | |
| 6,974,415 B2 | 12/2005 | Cerwin et al. | |
| 6,994,675 B2 | 2/2006 | Sharrock | |
| 7,001,338 B2 | 2/2006 | Hayek et al. | |
| 7,020,581 B2 | 3/2006 | Dittberner | |
| 7,028,861 B2 | 4/2006 | Sayers et al. | |
| 7,037,268 B1 | 5/2006 | Sleva et al. | |
| 7,044,922 B1 | 5/2006 | Dondysh | |
| 7,096,060 B2 | 8/2006 | Arand et al. | |
| D527,819 S | 9/2006 | Poulsen et al. | |
| 7,107,095 B2 | 9/2006 | Manolas | |
| 7,113,825 B2 | 9/2006 | Pastore et al. | |
| 7,123,962 B2 | 10/2006 | Siejko et al. | |
| 7,142,919 B2 | 11/2006 | Hine et al. | |
| 7,162,294 B2 | 1/2007 | Rowlandson et al. | |
| 7,174,203 B2 | 2/2007 | Arand et al. | |
| 7,190,994 B2 | 3/2007 | Mohler et al. | |
| 7,246,069 B1 | 7/2007 | O'Hanlon et al. | |
| 7,260,429 B2 | 8/2007 | Siejko et al. | |
| 7,285,095 B2 | 10/2007 | Ito et al. | |
| 7,289,634 B2 | 10/2007 | Grove | |
| 7,291,111 B2 | 11/2007 | Shertukde et al. | |
| 7,300,405 B2 | 11/2007 | Guion et al. | |
| 7,300,407 B2 | 11/2007 | Watrous | |
| 7,346,174 B1 * | 3/2008 | Smith .................... | 381/67 |
| 7,351,207 B2 | 4/2008 | Priemer | |
| 7,416,531 B2 | 8/2008 | Mohler | |
| 7,422,561 B2 | 9/2008 | Kanai et al. | |
| 7,458,939 B2 | 12/2008 | Munk | |
| 7,462,153 B2 | 12/2008 | Bostian et al. | |
| 7,477,936 B2 | 1/2009 | Hardahl et al. | |
| 7,515,948 B1 | 4/2009 | Balberg et al. | |
| 7,520,860 B2 | 4/2009 | Guion-Johnson et al. | |
| 7,527,597 B2 | 5/2009 | Sandler | |
| 7,611,471 B2 | 11/2009 | Thiagarajan et al. | |
| 7,621,875 B2 | 11/2009 | Pravica et al. | |
| 7,736,314 B2 | 6/2010 | Beach et al. | |
| 7,765,001 B2 | 7/2010 | Echt et al. | |
| 7,806,833 B2 | 10/2010 | Thiagarajan et al. | |
| 7,819,814 B2 | 10/2010 | Gavriely et al. | |
| 7,840,259 B2 | 11/2010 | Xue et al. | |
| 7,862,511 B2 | 1/2011 | Rafter | |
| 7,877,142 B2 | 1/2011 | Moaddeb et al. | |
| 7,963,925 B1 | 6/2011 | Schecter | |
| 7,981,058 B2 | 7/2011 | Akay | |
| 7,991,458 B2 | 8/2011 | Hardahl et al. | |
| 8,067,173 B2 | 11/2011 | Liew | |
| 8,110,358 B2 | 2/2012 | Liew | |
| 8,114,597 B2 | 2/2012 | Liew | |
| 8,133,674 B2 | 3/2012 | Liew | |
| 8,133,675 B2 | 3/2012 | Liew | |
| 8,148,072 B2 | 4/2012 | Liew | |
| 8,154,175 B2 | 4/2012 | Schmidt | |
| 8,157,742 B2 | 4/2012 | Taylor | |
| 8,600,488 B2 | 12/2013 | Mohler | |
| 9,526,430 B2 | 12/2016 | Srinivas | |
| 9,540,694 B2 | 1/2017 | Sukumar | |
| 9,572,497 B2 | 2/2017 | Razanksy | |
| 9,597,004 B2 | 3/2017 | Hughes | |
| 9,610,016 B2 | 4/2017 | Marmor | |
| 9,628,890 B2 | 4/2017 | Bibl | |
| 9,629,560 B2 | 4/2017 | Joseph | |
| 9,640,088 B1 | 5/2017 | Whitehurst | |
| 9,643,091 B2 | 5/2017 | Vock | |
| 9,646,137 B2 | 5/2017 | Gilley | |
| 9,649,042 B2 | 5/2017 | Albert | |
| 9,676,856 B2 | 6/2017 | Chen | |
| 9,693,759 B2 | 7/2017 | Seguy | |
| 9,699,546 B2 | 7/2017 | Qian | |
| 2001/0014162 A1 * | 8/2001 | Orten .................... | 381/67 |
| 2001/0027335 A1 | 10/2001 | Meyerson et al. | |
| 2002/0072684 A1 | 6/2002 | Stearns | |
| 2002/0095087 A1 | 7/2002 | Mourad et al. | |
| 2002/0133069 A1 | 9/2002 | Roberts | |
| 2002/0151795 A1 * | 10/2002 | Palti .................... | 600/454 |
| 2002/0156385 A1 | 10/2002 | Feng et al. | |
| 2003/0040675 A1 | 2/2003 | Sharrock | |
| 2003/0229289 A1 | 12/2003 | Mohler et al. | |
| 2004/0073094 A1 | 4/2004 | Baker | |
| 2004/0092846 A1 | 5/2004 | Watrous | |
| 2004/0106960 A1 | 6/2004 | Siejko et al. | |
| 2004/0106961 A1 | 6/2004 | Siejko et al. | |
| 2004/0127790 A1 | 7/2004 | Lang et al. | |
| 2004/0138567 A1 | 7/2004 | Ito et al. | |
| 2004/0236217 A1 | 11/2004 | Cerwin et al. | |
| 2004/0249293 A1 * | 12/2004 | Sandler et al. ............ | 600/481 |

(56) References Cited

U.S. PATENT DOCUMENTS

| | | |
|---|---|---|
| 2004/0260193 A1 | 12/2004 | LaSala |
| 2005/0038360 A1 | 2/2005 | Shertukde et al. |
| 2005/0090870 A1 | 4/2005 | Hine et al. |
| 2005/0137464 A1 | 6/2005 | Bomba |
| 2005/0157887 A1* | 7/2005 | Kim .............................. 381/67 |
| 2005/0177049 A1 | 8/2005 | Hardahl et al. |
| 2005/0222515 A1 | 10/2005 | Polyshchuk |
| 2005/0234313 A1 | 10/2005 | Rowlandson et al. |
| 2005/0240086 A1 | 10/2005 | Akay |
| 2005/0251047 A1 | 11/2005 | Sleva et al. |
| 2006/0025690 A1 | 2/2006 | Guigne et al. |
| 2006/0047213 A1 | 3/2006 | Gavriely et al. |
| 2006/0079773 A1 | 4/2006 | Mourad et al. |
| 2006/0079782 A1 | 4/2006 | Beach et al. |
| 2006/0134109 A1 | 6/2006 | Gaitanaris et al. |
| 2006/0161064 A1 | 7/2006 | Watrous et al. |
| 2006/0241527 A1 | 10/2006 | Muratore et al. |
| 2006/0245597 A1 | 11/2006 | Guion-Johnson et al. |
| 2007/0055151 A1 | 3/2007 | Shertukde |
| 2007/0055184 A1 | 3/2007 | Echt et al. |
| 2007/0078344 A1 | 4/2007 | Rafter |
| 2007/0167767 A1 | 7/2007 | Shertukde et al. |
| 2007/0191740 A1 | 8/2007 | Shertukde et al. |
| 2007/0208264 A1 | 9/2007 | Hardahl et al. |
| 2007/0239003 A1 | 10/2007 | Shertukde et al. |
| 2007/0258894 A1 | 11/2007 | Melker et al. |
| 2007/0282174 A1 | 12/2007 | Sabatino |
| 2008/0013747 A1 | 1/2008 | Tran |
| 2008/0039733 A1 | 2/2008 | Unver et al. |
| 2008/0040087 A1 | 2/2008 | Watrous |
| 2008/0051670 A1 | 2/2008 | Ballet et al. |
| 2008/0051840 A1 | 2/2008 | Moaddeb et al. |
| 2008/0058607 A1 | 3/2008 | Watrous |
| 2008/0077029 A1 | 3/2008 | Mohler et al. |
| 2008/0091090 A1 | 4/2008 | Guillory |
| 2008/0146934 A1 | 6/2008 | Czygan et al. |
| 2008/0154143 A1 | 6/2008 | Xue et al. |
| 2008/0255433 A1 | 10/2008 | Prough et al. |
| 2008/0287800 A1 | 11/2008 | Furman |
| 2008/0300487 A1 | 12/2008 | Govari et al. |
| 2008/0306367 A1 | 12/2008 | Koehler |
| 2009/0030324 A1 | 1/2009 | Kato et al. |
| 2009/0030471 A1 | 1/2009 | Rousso et al. |
| 2009/0093687 A1 | 4/2009 | Telfort et al. |
| 2009/0177107 A1 | 7/2009 | Guion-Johnson |
| 2009/0292309 A1 | 11/2009 | Maschke |
| 2009/0318802 A1 | 12/2009 | Boyden et al. |
| 2010/0016783 A1 | 1/2010 | Bourke, Jr. et al. |
| 2010/0030095 A1 | 2/2010 | Yu |
| 2010/0069767 A1 | 3/2010 | Hardahl et al. |
| 2010/0094152 A1 | 4/2010 | Semmlow |
| 2010/0103349 A1 | 4/2010 | Schmidt et al. |
| 2010/0106038 A1 | 4/2010 | Schmidt et al. |
| 2010/0145210 A1 | 6/2010 | Graff et al. |
| 2010/0160807 A1 | 6/2010 | Schmidt et al. |
| 2010/0210947 A1 | 8/2010 | Burcher et al. |
| 2010/0217125 A1 | 8/2010 | Kadokura et al. |
| 2010/0228140 A1 | 9/2010 | Hirsh |
| 2010/0249629 A1 | 9/2010 | Schmidt et al. |
| 2010/0312118 A1 | 12/2010 | Horzewski |
| 2011/0021970 A1 | 1/2011 | Vo-Dinh et al. |
| 2011/0029038 A1 | 2/2011 | Hyde et al. |
| 2011/0034831 A1 | 2/2011 | Christensen et al. |
| 2011/0105928 A1 | 5/2011 | Bojovic et al. |
| 2011/0137210 A1 | 6/2011 | Johnson et al. |
| 2011/0139594 A1 | 6/2011 | Schmidt |
| 2011/0306857 A1 | 12/2011 | Razansky et al. |
| 2012/0034624 A1 | 2/2012 | Miller et al. |
| 2012/0128223 A1 | 5/2012 | Hassan et al. |
| 2012/0209131 A1 | 8/2012 | Jones et al. |
| 2013/0137959 A1 | 5/2013 | Lisogurski et al. |
| 2013/0137960 A1 | 5/2013 | Lisogurski et al. |
| 2013/0211208 A1 | 8/2013 | Varadan et al. |
| 2013/0245448 A1 | 9/2013 | Kadokura |
| 2013/0261484 A1 | 10/2013 | Schmidt et al. |
| 2014/0180153 A1 | 6/2014 | Zia et al. |
| 2016/0367839 A1 | 12/2016 | Hoelscher |
| 2016/0372009 A1 | 12/2016 | Eggert |
| 2017/0011182 A1 | 1/2017 | Whitehurst |
| 2017/0049339 A1 | 2/2017 | Kapoor |
| 2017/0065186 A1 | 3/2017 | Joseph |
| 2017/0065188 A1 | 3/2017 | Jain |
| 2017/0078780 A1 | 3/2017 | Qian |
| 2017/0078781 A1 | 3/2017 | Qian |
| 2017/0078785 A1 | 3/2017 | Qian |
| 2017/0079581 A1 | 3/2017 | Walczak |
| 2017/0086686 A1 | 3/2017 | Narasimhan |
| 2017/0100062 A1 | 4/2017 | Marmor |
| 2017/0119255 A1 | 5/2017 | Mahajan |
| 2017/0135961 A1 | 5/2017 | Chandran |
| 2017/0185737 A1 | 6/2017 | Kovacs |
| 2017/0231597 A1 | 8/2017 | Howard |

FOREIGN PATENT DOCUMENTS

| | | |
|---|---|---|
| WO | WO2009080040 | 7/2009 |
| WO | WO2011/039329 | 4/2011 |
| WO | WO2011/071989 | 6/2011 |
| WO | WO2012/080209 | 6/2012 |
| WO | WO2012/107050 | 8/2012 |

OTHER PUBLICATIONS

Gaasch et al., "Ischemic Mitral Regurgitation", Last Literature Review—UpToDate Online Version 19.3: Sep. 2011/ This topic last updated: Oct. 14, 2011.

Garber et al., "Stress Testing for the Diagnosis of Coronary Heart Disease", Last Literature Review—UpToDate Online Version 19.3: Sep. 2011/ This topic last updated: Jun. 14, 2010.

International Search Report and Written Opinion for International Application No. PCT/US2010/059412 dated Aug. 26, 2011.

Akosah, KO., A.S. , Preventing Myocardical Infarction in the Young Adult in the First Place: How do the National Cholesterol Education Panel III Guidelines Perform?, J Am Coll Cardiol. 1475-1479. (2003).

American Heart Association. Cardiovascular Disease Statistics. Feb. 7, 2009 from: http://www.americanheart.ord/presenter.jhtml?identifier=4478.

American Heart Association. Heart Disease and Stroke Statistics: 2006 Update.

CDC-OC. Facts about Cardiovascular Disease: CDC-OC. Jun. 20, 2006.

Chambless, LE, H.G., Association of Coronary Heart Disease Incidence with Carotid Arterial Wall Thickness and Major Risk Factors: The Atherosclerosis Risk in Communities (ARIC) Study. Am. J. Epidemiol, pp. 483-494. (1997).

Clouse, M.E., "How Useful is Computed Tomography for Screening for Coronary Artery Disease? Noninvasive Screening for Coronary Artery Disease with Computed Tomography is Useful", Circulation, pp. 125-146. (2006).

Dock, W. Z. S, A Diastolic Murmur Arising in a Stenosed Coronary Artery. Am J Med., pp. 617-619. (1967).

Executive Summary of the Third Report of the National Cholesterol Education Program (NCEP) Expert Panel on Detection, Evaluation and Treatment of High Blood Cholesterol in Adults (Adult Treatment Panel III). (2001).

Freiherr, G., "Innovation Spurs Novel Nontradition Applications. Ultrasound Strengths Make it a Favorite Alternative for Initial Assessments", Diagnostic Imaging. vol. 30, No. 11. (2008).

Furberg, CD, H.C., " the 27th Bethesda Conference: Matching the Intensity of Risk Factor Management with the Hazard of Coronary Disease Events. Task Force 2: Clinical Edipemiology—the Coneptual Basis for Interpreting Risk Factors" J Am Col Cardiol., pp. 976-978. (1996).

Gaasch, W, O.C., Introduction to: Ischemic Mitral Regurgitation. Retrieved Nov. 10, 2011 from UpToDate, Online 19.2: http://www.uptodate.com/online/content/topic.do?topicKey=valve_hd/5714&selectedTitle=2~150&source-search_result.

(56) References Cited

OTHER PUBLICATIONS

Garber A, H.M. Introduction to: Stress Testing for the Diagnosis of Coronary Heart Disease UptoDate Online 19.2 USA. Nov. 10, 2011.
Garber AM, S.N., Cost-Effectiveness of Alternative Test Strategies for the Diagnosis of Coronary Artery Disease. Ann Intern Med., pp. 719-728. (1999).
Gibbons RJ, A.J., (n.d.) ACC/AHA 2002 Guideline Update for the Management of Patients with Chronic Stable Angina. Retrieved Mar. 23, 2009 from American College of Cardiology. Clinical Statements/Guidelines: www.acc-org/qualityandscience/clinical/statements.htm.
Grundy SM, P.R., "Assessment of Cardiovascular Risk by Use of Multiple-Risk-Factor Assessment Equations", Circulation, pp. 1348-1359 (1999).
Guion M., T.A., "Using Voice-Recognition Technology to Eliminate Cardiac Cycle Segmentation in Automated Heart Sound Diagnosis" Biomedical Instrumentation & Technology. (2007).
Guion, M, Computerized Heart Valve Diagnosis using a Digital Stethoscope. Dissertation. Minneapolis, MN USA: Universtiy of Minnesota, Graduate School. Apr. 2004.
Kannel WB, F.M., "Natural History of Angina Pectoris in the Framingham Study: Prognosis and Survival", Am J Cardiol., pp. 154-163. (1972).
Konstantino, Y.W., "Non-Traditional Biomarkers of Artherosclerosis in Stable and Unstable Coronary Artery Disease, Do They Differ?", Acute Cardiac Care, pp. 197-206. (2007).
Lee, TT, B.C., "Clinical Practice. Noninvasive Tests in Patient with Stable Coronary Artery Disease", N Engl J Med, pp. 1840-1845, (2001).
Mercuri M, M.D., "Non-invasive Imaging of Atherosclerosis" Springer. (1998). pp. 221-235.
Roeters Van Lennep JE, Z.A."Gender Differences in Diagnosis and Treatment of Coronary Artery Disease from 1981 to 1997. No Evidence for the Yentl Syndrome" European Heart Journal, pp. 911-918. (2000).
Semmlow J, R.K.,"Acoustic Detection of Coronary Artery Disease" Annu. Reve. Biomed. Eng., pp. 449-469, (2007).
Vasan RS, S.L.,"Relative Importance of Borderline and Elevated Levels of Coronary Heart Disease Risk Factors", Ann Intern Med., pp. 393-402, (2005).
W Rosamond, K, F.J.S., "Heart Disease and Stroke Statistics: 2007 update: A Report from the American Heart Association Committee and Stroke Statistics Subcommittee" Circulation, e69-e171., (2007).
Weiner DA, M.T., "Exercise Stress Testing: Correlations Among History of Angina, ST-Segment Response and Prevalence of Coronary-Artery Disease in the Coronary Artery Surgery Study (CASS)", N Engl J Med, pp. 230-235, (1979).
White CW, W.C., "Does Visual Interpretation of the Coronary Ateriogram Predict the Physiologic Importance of a Coronary Stenosis?". N Engl J Med, pp. 819 (1984).
Willerson JT, W.H., et al."Cardiovascular Medicine" London: Springer (2007). Chapters 34, 81 and 82.
Grundlehner, "Methods to Characterize Sensors for Capturing Body Sounds", 2011 International Conference of Body Sensor Networks. IEEE Computer Society., pp. 59-64 (2011).
Hansen et al., "System for Acquisition of Weak Murmurs Related to Coronary Artery Diseases", Department of Health Science and Technology. Denmark. 4 pages. http://www.cinc.org/2011/preprints/279.pdf retrieved Nov. 10, 2011.
Khan, "Thin Electronic Patches on Skin Could Monitor Hearts Comfortably", Los Angeles Times. 3 pages. Aug. 11, 2011.
Cost of Caring: Key Drivers of Growth in Spending on Hospital Care. Prepared by the American Hospital Assoc. and the Federation of American Hospitals. Feb. 19, 2003. pp. 1-20. Pricewaterhouse Coopers.
Cheng, "Diastolic Murmer Caused by Coronary Artery Stenosis", Annals of Internal Medicine 72:543-546. 1970.
Lloyd-Jones, et al., "Heart Disease and Stroke Statistics: 2009 update: A Report from the American Heart Association Committee and Stroke Statistics Subcommittee" Circulation, e21-e181., (2009).

Guion-Johnson, "Abstract 2866: Using Digital Stethoscope Data to Diagnose Stenosis in the Left Anterior Descending Coronary Artery" Circulation 2006. American Heart Association. Vascular Assessment and Intervention.
Application and File History for U.S. Appl. No. 11/402,654, filed Apr. 12, 2006, inventors Guion-Johnson et al.
Application and File History for U.S. Appl. No. 12/406,849, filed Mar. 18, 2009, inventors Guion-Johnson et al.
Application and File History for U.S. Appl. No. 12/962,812, filed Dec. 18, 2010, inventor Johnson.
Application and File History for Application No. PCT/US10/59412 filed Dec. 8, 2010 inventor Johnson.
Cheng, "Late Systolic Murmur in Coronary Artery Disease", Chest. pp. 346-356 vol. 61, No. 4. Apr. 1972.
Sangster et al., "Diastolic Murmur of Coronary Artery Stenosis" British Heart Journal. (35) pp. 840-844. 1973.
Stroud et al., "Numerical Analysis of Flow Through a Severely Stenotic Carotid Artery Bifurcation", Journal of Biomechanical Engineering. vol. 124. pp. 92-0. Feb. 2002.
Varghese et al., "Modeling Transition to Turbulence in Eccentric Stenotic Flows", School of Mechanical Engineering. Mar. 28, 2007.
Sherwin et al., "Three-Dimensional Instabilities and Transition of Steady and Pulsatile Axisymmetric Stenotic Flows", Journal of Fluid Mechanics. vol. 533 pp. 297-327. 2005.
Varghese et al., "Direct Numerical Simulation of Stenotic Flows", Part 1: Steady Flow. Journal of Fluid Mechanics. Jan. 28, 2005.
Varghese et al., "Direct Numerical Simulation of Stenotic Flows", Part 2: Steady Flow. Journal of Fluid Mechanics. Jan. 28, 2005.
Varghese et al., "Numerical Modeling of Pulsatile Turbulent Flow in Stenotic Vessels" Journal of Biomechanical Engineering. vol. 125 pp. 445-460. Aug. 2003.
Karri et al., "Time-Resolved DPIV Investigation of Pulsatile Flow in Symmetric Stenotic Arteries-Effects of Phase Angle". Journal of Biomechanical Engineering. vol. 132. Mar. 2010.
Akay et al.,. "Dynamics of the Sounds Caused by Partially Occluded Femoral Arteries in Dogs" Annals of Biomedical Engineering. vol. 22, pp. 493-500. (1994).
Akay et al., "Detection of Coronary Occlusions Using Autoregressive Modeling of Diastolic Heart Sounds", IEEE Transactions on Biomedical Engineering. vol. 34, No. 4. Apr. 1990.
Yazicioglu et al., "Acoustic Radiation from Fluid-filled, subsurface vascular tube with internal turbulent flow due to a constriction", The Journal of the Acoustical Society of America 118(2): 1193-1209. Aug. 2005.
Semmlow et al., "Noninvasive Detection of Coronary Artery Disease Using Parametric Spectral Analysis Methods" IEEE Engineering in Medicine and Biology Magazine. pp. 33-36. Mar. 1990.
Akay et al., "Noninvasive acoustical detection of coronary artery disease using the adaptive line enhancer method", Medical and Biological Engineering & Computing. pp. 147-154.
Xiao et al., "The Phonocardiogram Exercise Test", IEEE Engineering in Medicine and Biology. pp. 111-115. Jul./Aug. 1999.
Borisyuk, "Experimental Study of Noise Produced by Steady Flow through a Simulated Vascular Stenosis". Journal of Sound and Vibration. 256(3), pp. 475-498.(2002).
Akay et al.,"Analysis of Diastolic Heart Sounds Before and After Angioplasty", IEEE Engineering in Medicine and Biology Society 10th Annual International Conference. 1988.
Zhidong, "Noninvasive Diagnosis of Coronary Artery Disease Based on Instantaneous Frequency of Diastolic Murmurs and SVM". Engineering in Medicine and Biology 27th Annual Conference. 2005.
Yongchareon et al., "Initiation of Turbulence in Models of Arterial Stenoses". Journal of Biomechanics. vol. 12. pp. 185-189; 191-196.
Young et al., "Flow Characteristics in Models of Arterial Stenoses-I. Steady Flow" Journal of Biomechanics. vol. 6, pp. 395-410. 1973.
Young et al., "Flow Characteristics in Models of Arterial Stenoses-II. Unsteady Flow" Journal of Biomechanics. vol. 6, pp. 547-559. 1973.
Khalifa et al., "Characterization and Evolution of Poststenotic Flow Disturbances" Journal of Biomechanics. vol. 14, No. 5, pp. 279-296. 1981.

(56) References Cited

OTHER PUBLICATIONS

Goral-Wojicka et al., "On the Acoustic Phenomena Produced by Turbulence in the Flowing Blood", Journal of Med Phys and Eng. pp. 29-35. 2002.

Güler et al., "Order Determination in Autoregressive Modeling of Diastolic Heart Sounds", Journal of Medical Systems. vol. 20, No. 1. 1996.

Gould, "Quantification of Coronary Artery Stenosis in Vivo" Circulation Research. vol. 57, No. 3 Sep. 1985.

Ku, "Blood Flow in Arteries", Annu. Rev. Fluid Mech. 29:399-434. 1997.

Logan, "On the Fluid Mechanics of Human Coronary Artery Stenosis", IEEE Transactions on Biomedical Engineering. vol. 22, No. 4. Jul. 1975.

Mates et al., "Fluid Dynamics of Coronary Artery Stenosis", Circulation Research. vol. 42, No. 1. Jan. 1978.

Dodge et al., "Lumen Diameter of Normal Human Coronary Arteries", Influence of Age, Sex, Anatomic Variation, and Left Ventricular Hypertrophy or Dilation Circulation. vol. 86, No. 1, pp. 232-246. Jul. 1992.

Pijls et al., "Functional Measurement of Coronary Stenosis" Journal of the American College of Cardiology. 2012; vol. 59, No. 12.

2011/ACCF/AHA/SCAI Guideline for Percutaneous Coronary Intervention. Journal of the American College for Cardiology. 2011; vol. 58, No. 24.

Wilson et al., "Acoustical Detection of Coronary Stenosis in Humans: an Angiographic Validation Study", European Heart Journal. 2012:33 (abstract supplement).

ACC/AHA Guidelines for Exercise Testing: Executive Summary. A report of the American College of Cardiology/American Heart Association Task Force on Practice Guidelines (Committee on Exercise Testing) Circulation. 1997; 96:345-354.

ACCF/ASNC/ACR/ASE/SCCT/SCMR/SNM 2009 Appropriate Use Criteria for Cardiac Radionuclide Imaging. Journal of the American College of Cardiology. 2009; vol. 53, No. 25.

ACCF/SCAI/STS/AATS/AHA/HFSA/ACCT 2012 Appropriate Use Criteria for Coronary Revascularization Focused Update. J. Am.Coll.Cardiol. 2012.

Vranckx et al., "Coronary Pressure-Derived Fractional Flow Reserve Measurement" Recommendations for Standardization, Recording and Reporting as a Core Laboratory Technique. Proposals for Integration in Clinical Trials pp. 312-317. 2012.

Bech et al., "Fractional Flow Reserve to Determine the Appropriateness of Angioplasty in Moderate Coronary Stenosis: A Randomized Trial", Journal of the American Heart Association. Apr. 18, 2011.

Berger et al., "Long-Term Clinical Outcome After Fractional Flow Reserve-Guided Percutaneous Coronary Intervention in Patients with Multivessel Disease." Journal of the American College of Cardiology. 2005; vol. 46, No. 3.

DeBruyne et al., Fractional Flow Reserve: a review. Education in Heart. 2008.

Pijls et al., "Percutaneous Coronary Intervention of Functionally Nonsignificant Stenosis" Journal of the American College of Cardiology. 2007; vol. 49 No. 21.

Tonino et al., "Angiographic Versus Functional Severity of Coronary Artery Stenoses in the FAME study" Journal of the American College of Cardiology. 2010; vol. 55, No. 25.

Tonino et al., "Fractional Flow Reserve versus Angiography for Guiding Percutaneous Coronary Intervention" The New England Journal of Medicine. vol. 360, No. 3. Jan. 15, 2009.

Eagle et al., "Committee to Update the Guidelines on Perioperative Cardiovascular Evaluation for Noncardiac Surgery" American Heart Association. Powerpoint presentation. 2003.

Auerbach et al., "Assessing and Reducing the Cardiac Risk of Noncardiac Surgery", Circulation. Journal of the American Heart Association. 2006.

Russo et al., "Clinical Value of Multidetector CT coronary angiography as a preoperative screening test before non-coronary cardiac surgery" Cardiovascular Surgery. 2007.

Preoperative Cardiac Testing as accessed on Nov. 6, 2012 at http://openanesthesia.org/index.php?title=Preoperative_Cardiac_Testing_(Contr oversies).

Munguia et al., "Acoustical Detection of Venous Stenosis in Hemodialysis Patients using Principal Component Analysis" 32nd Annual International Conference of the IEEE. Aug. 31-Sep. 4, 2010.

Pal et al, "Data Mining approach for Coronary Artery Disease Screening" 2011 International Conference on Image Information Processing. 2011.

Zimmerman et al., "Acoustic Coupler for Acquisition of Coronary Artery Murmurs" Computing in Cardiology. 2011; 38: 209-212.

Brosh et al., "Pulse Transmission Coefficient: A Novel Nonhyperemic Parameter for Assessing the Physiological Significance of Coronary Artery Stenoses" Journal of the American College of Cardiology. 2002; vol. 39, No. 6.

Cooper, "Feasibilty of Passive Acoustic Detection of Coronary Artery Disease Utilizing Source Separation" Thesis submitted to the faculty of the Virginia Polytechnic Institute and State University in partial fulfillment of the requirements for the degree of Master of Science in Biomedical Engineering. Dec. 1, 2010.

O'Boyle et al., "Duplex Sonography of the Carotid Arteries in Patients with Isolated Aortic Stenosis: Imaging Findings and Relation to Severity of Stenosis" AJR:166, Jan. 1996.

Schmidt, "Detection of Coronary Artery Disease with an Electronic Stethoscope". Aalborg University. 2011.

Zhang et al., "Noninvasive Detection of Mechanical Prosthetic Heart Valve Disorder", Computers in Biology and Medicine. 2012.

911 Warning Signs of Heart Attack, Stroke & Cardiac Arrest accessed Nov. 5, 2012 at: http://www.heart.org/HEARTORG/Conditions/911-Warnings-Signs-of-a-Heart-attack_UCM_305346_SubHomePage.jsp.

Developing Leaders in Biomedical Technology Innovation as accessed Nov. 5, 2012 at http://biodesign.stanford.edu/bdn/index.jsp.

What are Coronary Heart Disease Risk Factors? National Heart Lung and Blood Institute as accessed on Nov. 5, 2012. http://www.nhlbi.nih.gov/health/health-topics/topics/hd/.

Yoshida et al., "Instantaneous Frequency Analysis of Systolic Murmur for Phonocardiogram", Engineering in Medicine and Biology Society. Proceedings 19th International Conference. 1997.

Winslow, "If Only Heart Attacks Were Predictable", The Wall Street Journal. 4 pages. Updated Apr. 16, 2012.

Notification Concerning Transmittal of International Preliminary Report on Patentability (Chapter I of the Patent Cooperation Treaty) for International Application No. PCT/US2010/059412 dated Jun. 21, 2012, 2 pages.

Welkowitz et al., A model for disturbed coronary artery flow with Phonocardiographic Verification. Cardiac Electrophysiology, Circulation and Transport, Makhon Tekhnologi le-Yisreal Tekniyon, Universitat Bern, Rutgers University. Proceedings in the 7th Henry Goldberg Workshop. May 13-17, 1990.

David N. Ku, Annual Review of Fluid Mechanics, Bol. 29:399-434, Jan. 1997.

Ortiz et al., "Coronary Artery Disease: Noninvasive Diagnosis", Proceedings 40th Annual Conference on Engineering in Medicine and Biology. Sep. 10-13, 1987. Niagara Falls, NY.

Guion et al., "Diagnosing Stenosis in the left Anterior Descending Coronary Artery using Sound Math", Department of Mechanical Engineering Institute of Technology. Nov. 2006.

http://rfumsphysiology.pbworks.com/Heart-Sounds last revised on Jun. 15, 2006.

Chinese Office Action dated Apr. 11, 2014 for Chinese Application No. 201088063793.1.

T.O. Cheng, "Murmurs in Coronary-Artery Disease," New England Journal of Medicine, vol. 283, No. 16, pp. 1054, Oct. 15, 1970.

P.F. Cohn et al., "Diastolic Heart Sounds and Filling Waves in Coronary Artery Disease," Circulation, vol. XLIV, pp. 196-202, Jul.-Dec. 1971.

J. Manolas, "Noninvasive Detection of Coronary Artery Disease by Assessing Diastolic Abnormalities During Low Isometric Exercise," Clinical Cardiology, vol. 16, No. 3, pp. 205-212, Mar. 1993.

(56) References Cited

OTHER PUBLICATIONS

V. Padmanabhan et al, "Dynamical Analysis of Diastolic Heart Sounds Associated with Coronary Artery Disease," Annals of Biomedical Engineering, vol. 22, No. 3, pp. 264-271, 1994.

M. Akay, "Noninvasive Diagnosis of Coronary Artery Disease Using a Neural Network Algorithm," Biological Cybernetics, vol. 67, No. 4, pp. 361-337, 1992.

J. Semmlow et al., "Coronary Artery-Disease-Con-elates Between Diastolic Auditory Characteristics and Coronary Artery Stenoses," IEEE Transactions on Biomedical Engineering, vol. 30, No. 2, pp. 136-139, Feb. 1983.

O. Tateishi, "Clinical Significance of the Acoustic Detection of Coronary Artery Stenosis," J. Cardiol, vol. 38, No. 5, pp. 255-262, Nov. 2001.

M. Akay et al., "Noninvasive Detection of Coronary Stenoses Before and After Angioplasty Using Eigenvector Methods," IEEE Transactions on Biomedical Engineering, vol. 37, No. 11, pp. 1095-1104, Nov. 1990.

M. Akay et al., "Application of the ARMA Method to Acoustic Detection of Coronary Artery Disease," Medical & Biological Engineering & Computing, vol. 29, No. 4, pp. 365-372, Jul. 1991.

M. Akay et al., "Application of Adaptive Filters to Noninvasive Acoustical Detection of Coronary Occlusions Before and After Angioplasty," IEEE Transactions on Biomedical Engineering, vol. 39, No. 2, pp. 176-184, Feb. 1992.

M. Akay et al., "Acoustical Detection of Coronary Occlusions Using Neural Networks," Journal of Biomedical Engineering, vol. 15, No. 6, pp. 469-473, Nov. 1993.

Y. Akay et al., "Noninvasive Acoustical Detection of Coronary Artery Disease: A Comparative Study of Signal Processing Methods," IEEE Transactions on Biomedical Engineering, vol. 40, No. 6, pp. 571-578, 1993.

M. Akay et al., "Noninvasive Characterization of the Sound Pattern Caused by Coronary Stenosis Using FTF/FAEST Zero Tracking Filters: Normal/Abnormal Study," Annals of Biomedical Engineering, vol. 21, No. 2, pp. 175-182, Mar./Apr. 1993.

M. Akay et al., "Application of Adaptive FTF/FAEST Zero Tracking Filters to Noninvasive Characterization of the Sound Pattern Caused by Coronary Artery Stenosis Before and After Angioplasty," Annals of Biomedical Engineering, vol. 21, No. 1, pp. 9-17, Jan./Feb. 1993.

J.S. Karliner, "Noninvasive Evaluation of the Patient with Suspected Coronary Artery Disease," Current Problems in Cardiology, vol. 3, No. 4, pp. 1-66, Jul. 1978.

H. Sherman et al., "Computer-Assisted Diagnosis in Noninvasive Evaluation of Coronary Artery Disease," Journal of the American College of Cardiology, vol. 3, No. 2, Part 1, pp. 465-466, Feb. 1984.

J.Z. Wang et al., "Modeling Sound Generation in Stenosed Coronary Arteries," IEEE Transactions on Biomedical Engeering, vol. 37, No. 11, pp. 1087-1094, Nov. 1990.

* cited by examiner

Frequency (Hz)

DETECTION OF CORONARY ARTERY DISEASE USING AN ELECTRONIC STETHOSCOPE

This application is a continuation of U.S. patent application Ser. No. 11/402,654, filed Apr. 12, 2006, which claims the benefit of U.S. Provisional Application No. 60/670,905, filed Apr. 13, 2005, the entire contents of which are incorporated herein by reference.

TECHNICAL FIELD

The invention relates to medical diagnostic devices and, more particularly, electronic stethoscopes.

BACKGROUND

Coronary artery disease affects the lives of millions of people, and may affect the health of a patient without warning. Detection of coronary artery stenosis involves patient history, physical examination, stress testing and possibly a coronary angiogram. Beyond history and physical examination, the diagnostic technique is associated with significant cost and risk. Although the stress test is the most frequently ordered test to detect possible coronary artery disease, sensitivity and specificity of the stress test vary greatly from 40 percent to 90 percent, depending upon whether there is single or multi-vessel disease.

During routine physical examination in a clinic office, physicians and other medical providers use a stethoscope. It is inexpensive, easily portable, relatively comfortable, and safe. Advancements in digital technology have led to the production of electronic stethoscopes that can amplify sound, record patient data and transmit data to a computer for further processing. The transmitted data can be used to plot a phonocardiogram, improve patient records and even perform automated heart sound diagnosis.

Within the electronic stethoscope, an acoustic sensing device is employed to transmit the raw sound data from the patient to electronics within the stethoscope. The raw data from these sensors contains a plethora of acoustic information emanating from the thorax that includes not only heart valve and lung sounds but also acoustic information within the stethoscope sampling frequency and signal to noise ratio. Once in digital form, the data from the stethoscope sensor is filtered so that it sounds like a mechanical stethoscope.

SUMMARY

The invention is directed to an electronic stethoscope system that detects coronary artery disease in patients. The system uses an electronic stethoscope to record acoustic data from the chest. A processing technique is applied to the data in order to produce Fast Fourier Transform (FFT) data of magnitude versus frequency.

If a bell curve is identified in the data within a predefined frequency range with a peak magnitude of greater than a predefined threshold, the system produces an output to indicate that the patient is likely to have 50 to 99 percent blockage, or stenosis, in the coronary artery. As described herein, it has been identified that a blockage exceeding 50 percent manifests in a bell curve in the range of 50-80 Hz within the FFT data. As a result, in one embodiment, the system automatically determines that the patient is likely have 50 to 99 percent blockage, or stenosis, in the coronary artery when a bell curve is identified on the graph between 50 and 80 Hz with a peak magnitude of greater than 2.5 units. If no bell curve is present, the patient may have stenosis of less than 50 percent in the coronary artery.

Since artery stenosis can be left undetected until blood flow is severely restricted within the artery, a quick and non-invasive technique described herein would greatly increase the number of diseased patients that could be identified before their health deteriorates. Implementing the described processing methods into an electronic stethoscope may allow early warning for patients without disease symptoms. Positively identified patients could then participate in more invasive techniques to specifically identify the extent of the disease. This technique may also assist in preventing normal patients from having unnecessary expensive and dangerous techniques, i.e. angiography, performed.

In one embodiment, the invention provides method for detecting coronary artery disease using a stethoscope comprising placing an acoustic sensor over the fourth left intercostal space of a patient's chest, recording acoustic data from the acoustic sensor, applying one or more filters to the acoustic data and calculating a Fast Fourier Transform (FFT) of the data to produce FFT data, and automatically analyzing the FFT data to identify a bell curve within a predefined frequency range indicative of coronary artery disease.

In another embodiment, the invention provides an electronic stethoscope comprising an acoustic sensor, a memory that stores acoustic data from the acoustic sensor and instructions for processing the acoustic data, and a processor that processes the acoustic data to identify a bell curve in FFT data between a predefined frequency range indicative of coronary artery disease.

Although the invention may be especially applicable to detecting left anterior descending coronary artery stenosis, the invention alternatively may be applied to blockages in other arteries or the phenomenon of restinosis after a stent has been implanted to open the artery.

In various embodiments, the invention may provide one or more advantages. For example, the use of an electronic stethoscope to diagnose coronary artery disease may allow any patient to be screened due to the widespread use of electronic stethoscopes and the little amount of time this technique would require. During a routine physical examination, a physician may decide to perform this technique with only the equipment on his person and a few minutes of time. The physician may decide to have the system automatically produce a diagnosis based upon the processed data, or the physician may choose to print the data from a local computer to analyze the FFT graphed data himself.

This technique to identify coronary artery disease may also benefit patients who would normally be subjected to inaccurate stress testing or invasive angiography. Some patients with less than 50 percent artery occlusion, who would have been subjected to one of these tests, would be cleared of any addition testing. This may save patients from possible pain, injury, procedural costs, and unnecessary time. Strained health care facilities may also save personnel time and procedural costs.

In addition, the patient may modify the parameters of the processing technique to accommodate a variety of patients. An external module may be used to communicate with the electronic stethoscope to modify settings or upload updated processing tools. The external module may also be used to download data from the electronic stethoscope, transfer data to a general purpose computer, and recharge the battery of the electronic stethoscope.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
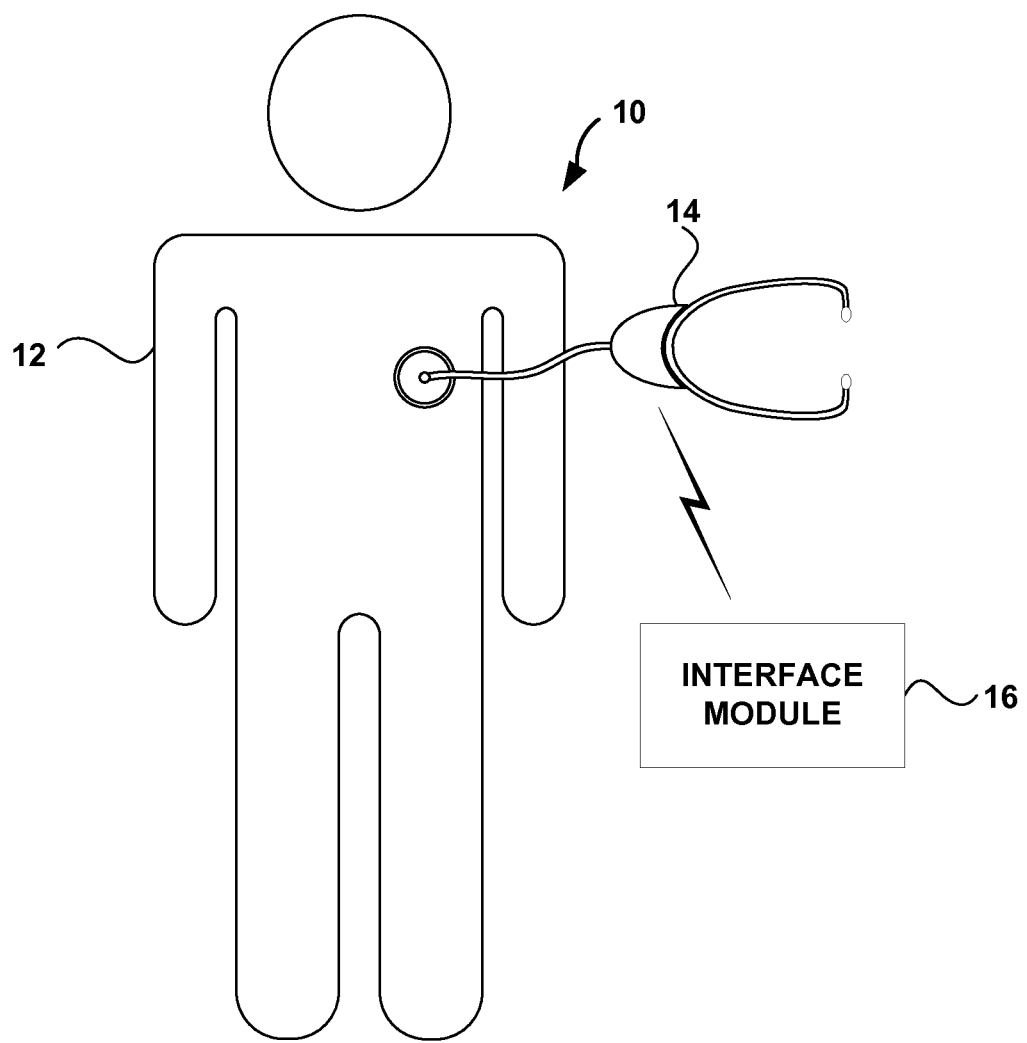
FIG. 1 is a schematic diagram illustrating an electronic stethoscope system placed on the chest of a patient to diagnose coronary artery disease.

FIG. 1 is a schematic diagram illustrating an electronic stethoscope system 10 to diagnose coronary artery disease. In the example of FIG. 1, system 10 includes an electronic stethoscope 14 applied to the chest of patient 12. Electronic stethoscope 14 may communicate with interface module 16, which may be internal or external to stethoscope 14, in order to transfer data from stethoscope 14 to a general purpose computer (either wirelessly or via conventional wired communication) or to modify diagnosis parameters of stethoscope 14.

With reference to FIG. 1, electronic stethoscope 14 includes an acoustic sensor, earphones, and an electronic processing element. The acoustic sensor is located at the distal, or patient, end of stethoscope 14. This sensor turns sound waves created within patient 12 into electrical signals that may be used by the stethoscope. Various types of sensors that may be used include microphones or piezoelectric crystals, or any sensor capable of detecting audible or inaudible vibrations associated with hemodynamics or arterial elasticity in the coronary arteries. In some embodiments, a plurality of acoustic sensors may be implemented to acquire patient data. The acoustic data may be filtered or amplified before reaching the earphones located at the proximal, or physician, end of electronic stethoscope 14. The physician may be able to modify the sound by adjusting the volume or certain frequencies.

The acoustic sensor of stethoscope 14 may be placed on the chest of patient 12. In particular, the acoustic sensor may be placed over the fourth left intercostal space. As blood flows through arteries, blockages within an artery lumen may cause the blood flow profile to change from laminar flow to turbulent flow as the blood passes faster over these obstructions. This turbulent flow produces sounds capable of being detected by the sensor within stethoscope 14. From this fourth left intercostals space, the sounds most applicable to coronary artery stenosis are audible from the chest. In some embodiments, other locations may be more appropriate when attempting to record acoustic data from this or other arteries.

The electronic processing element of electronic stethoscope 14 controls the function of the stethoscope. Acoustic data covering systole and diastole is acquired from the acoustic sensor, at which time the analog signal may be amplified or modified for listening by the physician. The signal is sent in real time to the earphones of the stethoscope for patient diagnosis purposes. While the signal is sent to the earphones, it may also be recorded within the processing element. Acoustic data may be stored in the memory for off-line analysis.

In this embodiment, the acoustic data recorded by stethoscope 14 may be downloaded by interface module 16. Communication between stethoscope 14 and interface module 16 may be accomplished through a Universal Serial Bus (USB) connection, IEEE 1394 connection, wireless telemetry connection, or some other transfer connection. Interface module 16 may then transfer the data to a general purpose computer, i.e. a desktop, notebook, or hand-held computer. The data may then be processed using computational software, i.e. MATLAB, to generate data for diagnosis. This data may be viewed on a screen, transferred to another computing device, or printed on paper. The physician may then make a diagnosis of the patient.

In some embodiments, acoustic data may be processed within the processing element. When desired by the physician, stethoscope 14 may automatically process the acoustic data and make a recommended diagnosis of the patient. By following the diagnosis technique to analyze the processed data, stethoscope 14 may present the diagnosis information through an LED indicator, LCD screen, or audio message to the physician. In this manner, the physician may be able to quickly analyze the acoustic data without the use of multiple devices. In addition to the automated diagnosis, the physician may have the option of manually analyzing the data as well.

In other embodiments, acoustic data may be automatically processed by sending acoustic data from stethoscope 14 to interface module 16. Data processing and analyzing may occur at this module or a host computer to conserve battery life or improve processing speed. The recommended diagnosis may then be delivered to the physician through a user interface on module 16 or the host computer.

Some embodiments of electronic stethoscope 14 may be able to monitor a variety of patient information and suggest a coronary artery analysis based upon certain indicators. In this case, stethoscope 14 may be able to assist the physician in detecting artery blockages or in-stent restenosis in patients with limited signs or symptoms.

Figure 2:
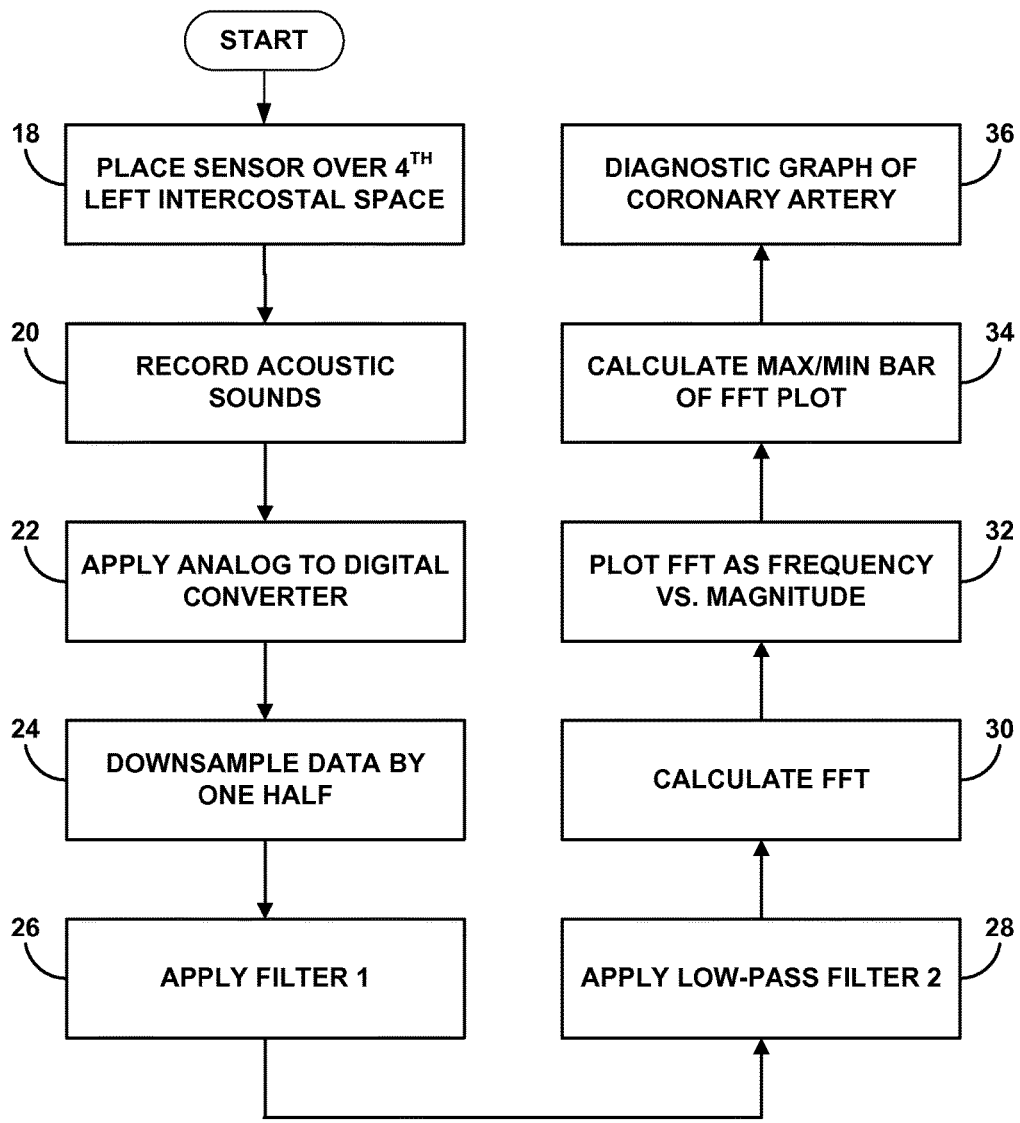
FIG. 2 is functional block diagram illustrating the method to record and process acoustic data from the stethoscope.

FIG. 2 is a functional block diagram illustrating the method to record and process acoustic data from stethoscope 14. The technique begins when the physician turns on electronic stethoscope 14. Once initiated, the acoustic sensor of stethoscope 14 is placed over the fourth left intercostal space of the chest (18). Once positioned, stethoscope 14 begins recording acoustic sounds produced over systole and diastole within the chest (20). Stethoscope 14 begins processing the signal by applying an analog to digital converter to produce digital data representative of an acoustic signal (22). Next, stethoscope 14 downsamples the digital data by one half to create a manageable data set (24). Stethoscope 14 also applies a first filter ("Filter 1") to the data in order to remove non-stenosis frequencies from the data (26), after which the stethoscope applies a low-pass filter ("Filter 2") to the data to eliminate frequencies above 100 Hz (28). Then, stethoscope 14 calculates a Fast Fourier Transform (FFT) of the data (30), in which the resultant FFT data may analyzed and/or graphically plotted with frequency on the x-axis and magnitude on the y-axis (32). Fourier analysis is based on the concept that signals can be approximated by a sum of sinusoids, each at a different frequency. Plotting the harmonic magnitudes on the y-axis (no units) and the frequency of the harmonic on the x-axis (Hz) generates a frequency spectrum. The spectrum is represented as a set of vertical lines or bars. The frequency has units of Hz and the magnitude has non-dimensional units. It can therefore also be referred to as a coefficient. Stethoscope 14 may then calculates a maximum and minimum bar from the FFT plot (34) and produces diagnostic data for the coronary artery (36).

For exemplary purposes, this functional block diagram shows the process stethoscope 14 would use to automatically process acoustic data for the diagnosis of coronary artery disease. In some embodiments, this process may be performed automatically by interface module 16 or manually by a clinician or technician with the aid of a personal computer.

Figure 3:
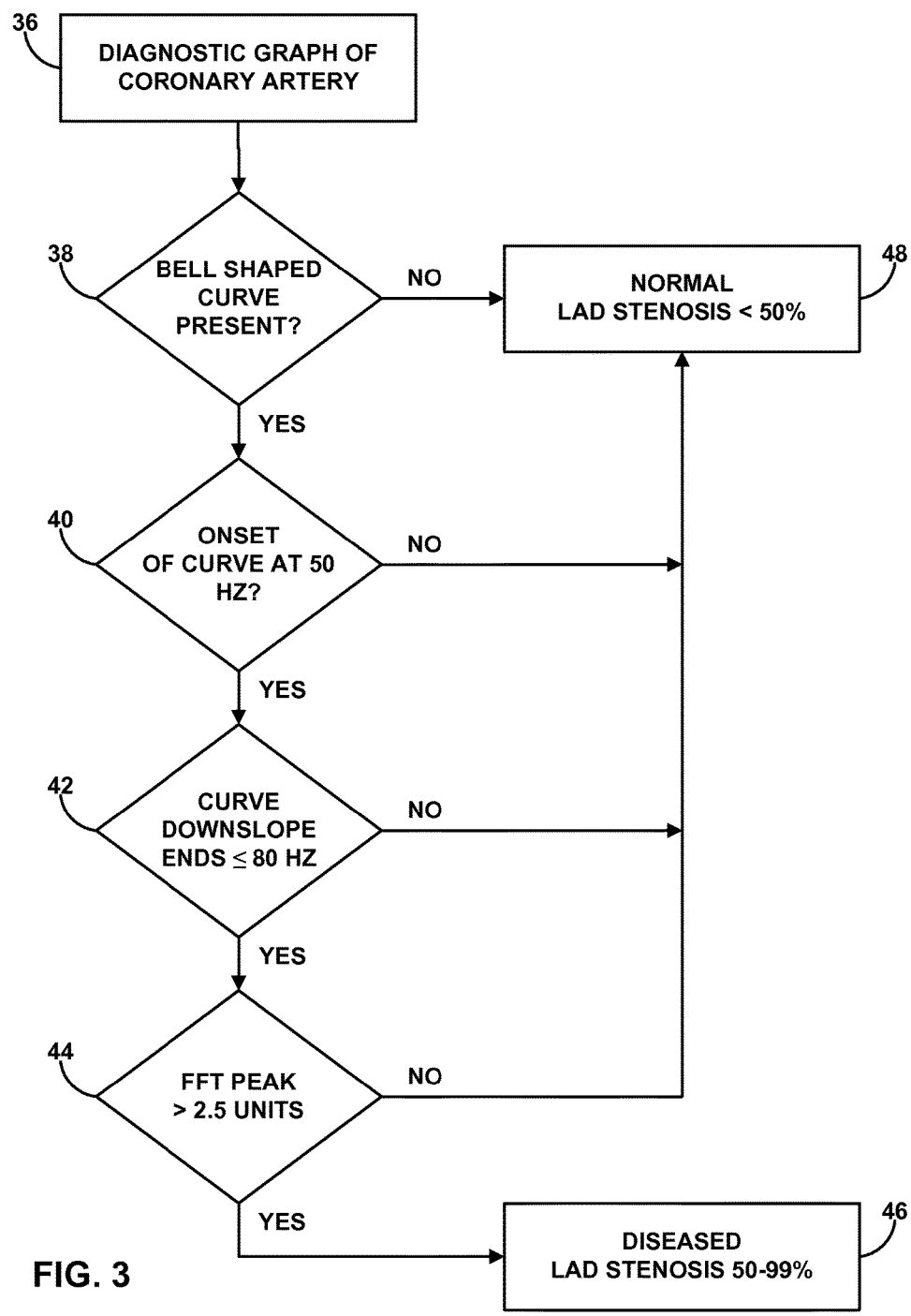
FIG. 3 is functional block diagram illustrating the method to diagnose coronary artery stenosis from the processed acoustic data.

FIG. 3 is a functional block diagram illustrating an exemplary method in which stethoscope 14 automatically diagnoses coronary artery stenosis from the processed acoustic data.

The diagnostic data containing the coronary artery data (36) needs to be analyzed for indications of stenosis. This may be done manually by a clinician or automatically by stethoscope 14, as illustrated by this example. First, stethoscope 14 determines whether a bell shaped curve exists within a particular spectral region of the FFT data (38). In particular, the stethoscope 14 determines whether the onset of the curve (i.e., the lower frequency where the upslope of the curve rises) occurs substantially at or closely after 50 Hz (40). If this is true, stethoscope determines whether the downslope of the bell shaped curve ends substantially at or before 80 Hz, i.e., that the bell shaped curve is bounded by this spectral region (42). If so, stethoscope 14 determines whether the FFT peak of the bell curve bounded by this region exceeds than 2.5 units (44). If all four of these criteria are met, stethoscope 14 (or interface module 16) outputs an indicator, e.g., a message, that the Left Anterior Descending (LAD) portion of the coronary artery is likely to have more 50 to 99 percent stenosis preventing blood flow and that coronary disease may be present. (46). If one or more of the presented criteria is not satisfied, then the stethoscope outputs an indicator, e.g., message, that the patient is likely to have less than 50 percent of the LAD portion of the coronary artery blocked (48).

For exemplary purposes, this functional block diagram shows the process stethoscope 14 would use to automatically diagnose coronary artery disease from processed acoustic data. In some embodiments, this process may be performed automatically by interface module 16 or manually by a clinician or technician with the aid of a personal computer. In the cases of manual diagnosis, the FFT data may be graphed or plotted for the clinician to observe the data as a whole, and the identified bell curve may be highlighted or colored differently from the other portions of the graph. For example, a bell shaped group of data would be identifiable between 50 and 80 Hz on the graph in the case of a patient with greater than 50 percent artery stenosis.

In some embodiments, the criteria described in FIG. 3 may be determined in different order. For example, after the bell shaped curve is identified in block 38, the next criteria of the curve identified may be a FFT peak of greater than 2.5 units as shown in block 44. While each criterion is assessed to determine which indicator to output relative to the likely presence of LAD stenosis, the order in which they are assessed is not as critical.

In other embodiments, certain criteria may indicate a particular percentage of stenosis and enable the diagnosis to separate a patient into more than two diseased states. A more sensitive diagnosis indicating more percentage levels of stenosis may allow for certain patients to wait before undergoing treatment while patients diagnosed with a greater percentage of stenosis would be urged to have immediate surgical intervention.

In other embodiments, LAD coronary artery stenosis may be detected through a slightly different method. Calculating the sum of the energy under the bell curve described above may allow the stethoscope to present an interval of probability of 50 to 99 percent stenosis. Calculating the energy from the data may enable more accurate diagnoses. Further, the summed energy information may allow the stethoscope to provide increased separation of the degree of stenosis. For example, the patient may be identified as likely having 25 to 50 percent, 50 to 75 percent, or 75 to 99 percent stenosis of the LAD or alternate portion of the coronary artery. This information may be beneficial to both the patient and physician.

In addition, the specific numerical indicators for detecting stenosis in the LAD may vary depending on the condition of the patient. For example, the FFT peak in block 44 may be greater than 2.5 units to indicate stenosis over 50 percent patients over 60 years of age, whereas the FFT peak in block 44 may be greater than 3 units to indicate stenosis over 50 percent in patients younger than 60 years of age. Factors such as age, gender, height, weight or history may be used in determining the exact criteria numbers. In general, the exact coefficients used in these criteria may be modified to best match the patient.

This technique may be particularly useful for initial screening of patients for LAD stenosis indicating coronary artery disease during a routine exam with a primary care physician. Patients failing to meet every criterion would not need further tests until at some time they show stenosis greater than 50 percent. Patients diagnosed with LAD stenosis greater than 50 percent may be directed toward further testing, such as an angiogram or angioplasty.

Various embodiments of the described invention may include processors that are realized by microprocessors, Application-Specific Integrated Circuits (ASIC), Field-Programmable Gate Arrays (FPGA), or other equivalent integrated logic circuitry. The processor may also utilize several different types of storage methods to hold computer-readable instructions for the device operation and data storage. These memory and storage media types may include a type of hard disk, random access memory (RAM), or flash memory, e.g. CompactFlash or SmartMedia. Each storage option may be chosen depending on the embodiment of the invention.

EXAMPLES

FIGS. 4 through 8 illustrate some of the results of the disclosed technique for diagnosing coronary artery stenosis when performed on patients that were already scheduled for a routine coronary angiogram due to typical symptoms or a positive stress test. Patients were excluded from this study if they had prior coronary artery bypass or cardiac transplant surgery, persistent atrial fibrillation, or any type of cardiac device including pacemakers and prosthetic valves.

To objectively quantify stenosis, angiographic data was collected from the final angiographic report. Coronary artery stenosis was classified as 25-50 percent, 50-75 percent, 75-90 percent, and 90-99 percent occlusion pre-intervention at the referral center. Data from 55 random patients was collected (age range 29-84, mean 57; 30 female, 25 male, Body Mass Index range 21-50, mean 30). Seventeen patients had normal angiograms, 6 had stenosis in coronary arteries other than the LAD, 11 had 25-50 percent stenosis, 5 had 50-75 percent stenosis, 5 had 75-90 percent stenosis, and 7 had 90-99 percent stenosis. A 41 year-old patient tested positive for pregnancy, another patient was diagnosed with MoyaMoya disease (had diffuse coronary spasm), a third patient refused the angiogram after being enrolled, and a fourth patient had a stent previously placed. All four patients were removed from our study.

A Littmann Model 4000 electronic stethoscope with recording frequencies within the human range of hearing (20-4000 Hz) was used to collect the data. This stethoscope can record a maximum of eight seconds of acoustic data per recording. Eight second recordings were collected at the 4th left intercostals space of a supine patient. A pre-angiogram was first taken and if the patient had an angioplasty, the same stethoscope was used to collect data post-angioplasty.

The 4lics thorax sounds were sampled as a series of voltages representing the sound amplitude of the acoustic signature. A filter was applied to the data to remove frequency information not related to stenosis in the LAD. A lowpass filter was then applied to the signal to eliminate noise and narrow the bandwidth to less than 100 Hz. The techniques included an analysis of acoustic information within the 20-100 Hz range of both the systolic and diastolic segments of the cardiac cycle. The frequency range and use of the entire cardiac cycle was used.

Using MATLAB 6.5, Release 13 (a program used from numeric computation and visualization) a Fast Fourier Transform (FFT) was calculated on the filtered data. A max-min bar was calculated for the resulting FFT data. The max-min bar was chosen so that variability between coefficient magnitudes and frequencies could be examined. Finally, the x-axis was plotted on a logarithmic scale for the 20-100 Hz frequency range.

Interpretation of the graph resulting from the analysis was based on a assessment of four graphical elements: 1) presence of a bell-shaped curve resulting from the variability between coefficient magnitudes and frequency, 2) onset of the bell-shaped curve at 50 Hz, 3) downslope of the bell-shaped curve ends ≤80 Hz, and 4) FFT peak coefficient magnitudes greater than 2.5 units (absolute scale for all analyses) at the maximum of the bell-shaped curve. If all four criteria are met, then the patient was identified to have 50-99 percent stenosis in the LAD. If all four criteria are not met, then the patient was identified as normal.

The graphs of FIGS. 4-8 compares data from real patients with and without coronary artery disease as determined through an angiogram, the current standard in conventional diagnosis. In the case of patients receiving intervention to rectify their disease, data was acquired before the angiogram and after the angioplasty. The same stethoscope was used for each diagnosis of a single patient.

Figure 4:
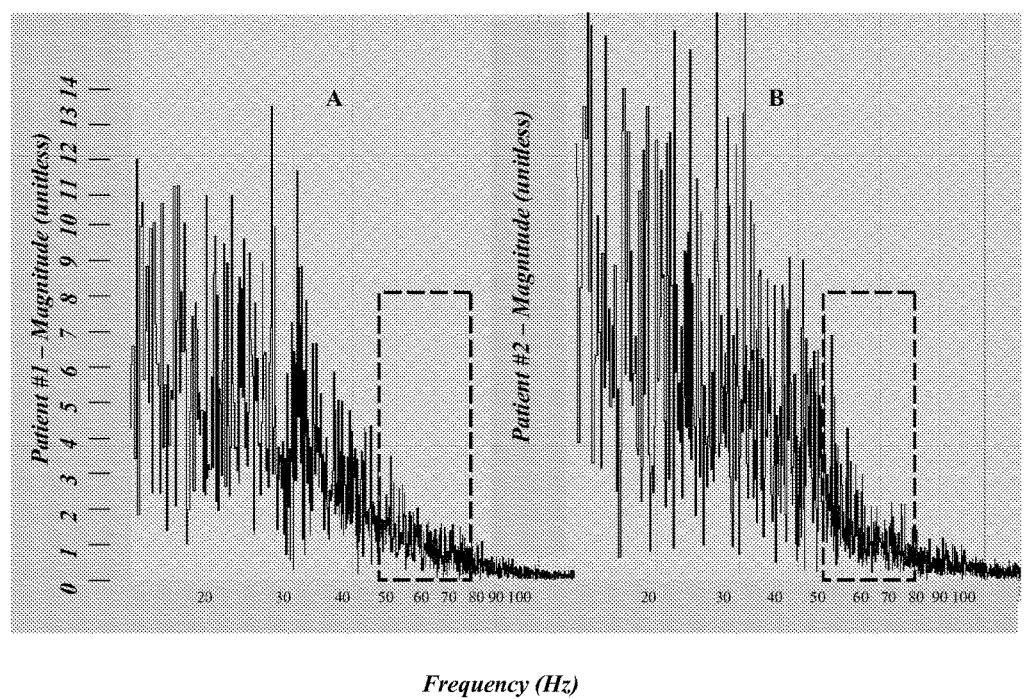
FIG. 4 shows data charts from two separate normal patient data sets after processing is completed.

FIG. 4 shows data charts generated for two separate normal patient data sets after processing is completed. The FFT graphical result shows normal coronary arteries between 0 and 100 Hz. The 50 to 80 Hz frequency bands associated with suspected LAD stenosis are highlighted with a rectangular box. As seen in graphs A and B, the coefficient magnitude decays with increasing frequency. In this example, there is no bell-shaped curve, so peak magnitude is irrelevant and the data fails to meet the criteria set forth in FIG. 3.

Figure 5:
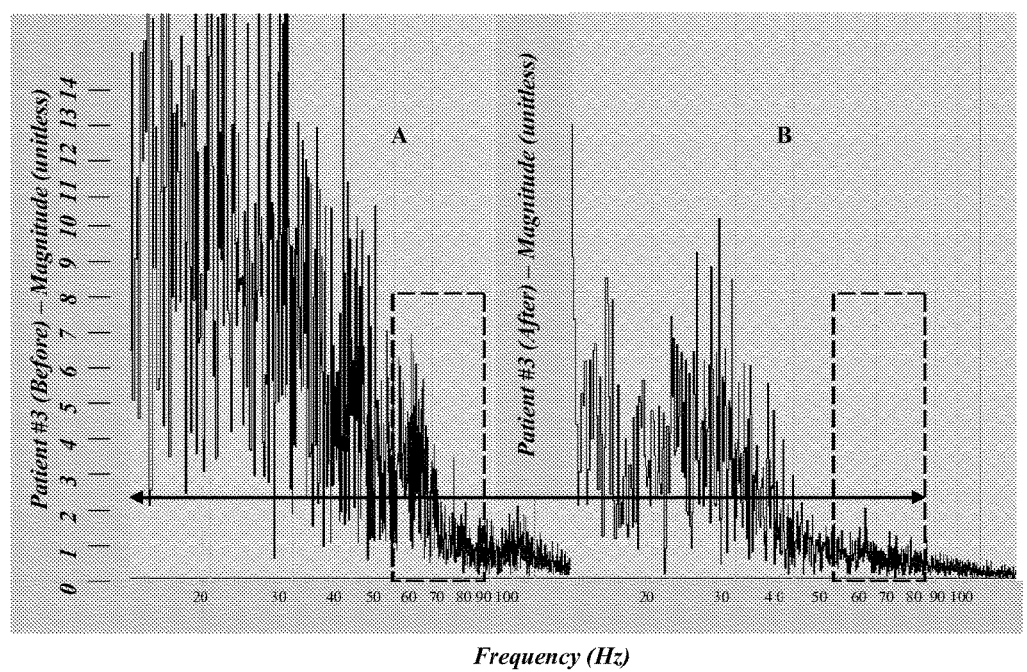
FIG. 5 shows data charts from a patient with 90-99% artery stenosis. Graph A shows pre-angiogram data, and graph B shows post-angioplasty data.

FIG. 5 shows data charts from a patient confirmed to have 90 to 99 percent artery stenosis in the proximal LAD. Graph A shows pre-angiogram data, and graph B shows post-angioplasty data. In this graph, the bell-shaped curve that may be associated with LAD stenosis was detected as shown. The bell-shaped curve upslope begins at 50 Hz and the downslope ends near 65 Hz. The maximum coefficient magnitude is greater than 2.5 units and is found at 55 Hz, the peak of the bell-shaped curve. The bell-shaped curve disappeared after angioplasty or stenting of the LAD. In this manner, Graph B of the patent taken post angioplasty is similar to a graph of a normal patient.

Figure 6:
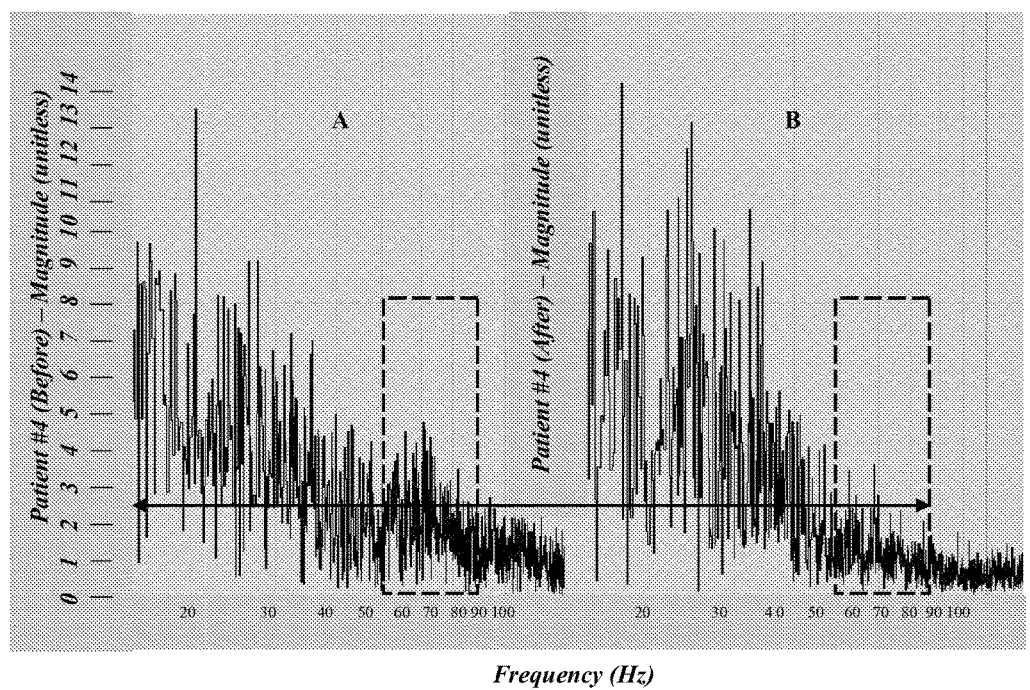
FIG. 6 shows data charts from a patient with 50-75% artery stenosis. Graph A shows pre-angiogram data, and graph B shows post-angioplasty data.

FIG. 6 shows data charts from a patient confirmed to have 50 to 75 percent stenosis in the first diagonal branch of the LAD. Graph A shows pre-angiogram data, and graph B shows post-angioplasty data. LAD stenosis was identified with the bell-shaped curve in the middle of the 50 to 80 Hz frequency range, and then confirmed via an angiogram. In this case, the maximum coefficient peak was greater than 2.5 units at approximately 65 Hz and decays to 80 Hz. A single drug-eluting stent was placed during angioplasty of this patient. Again, the techniques correctly identified a patient with a diseased coronary artery.

Figure 7:
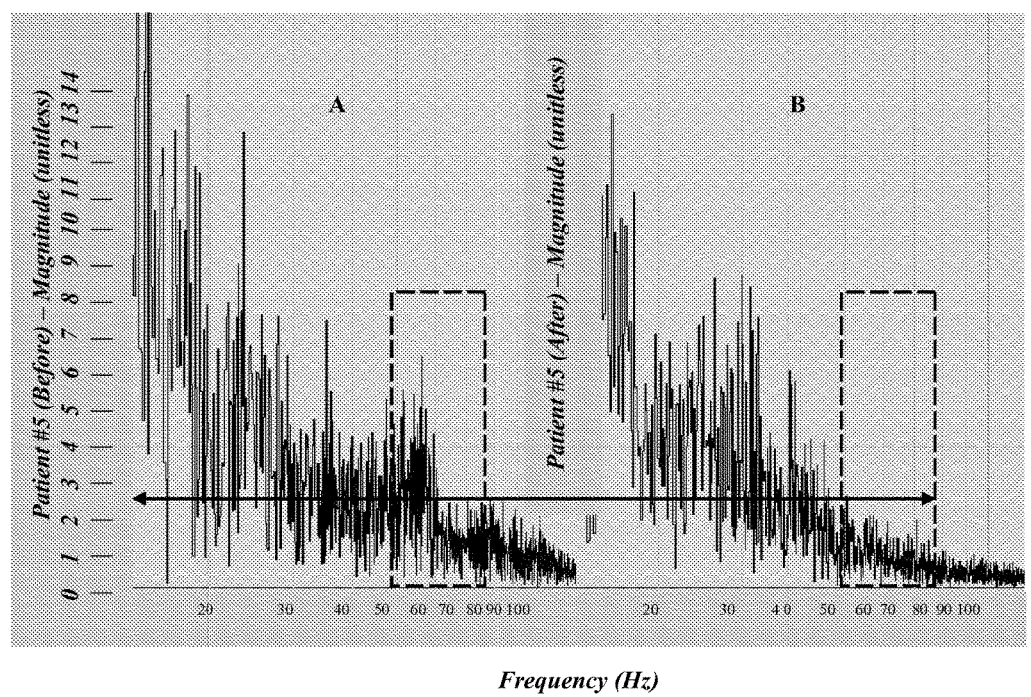
FIG. 7 shows data charts from a patient with 75-90% and 100% artery stenosis in different artery sections. Graph A shows pre-angiogram data, and graph B shows post-angioplasty data.

FIG. 7 shows data charts from a patient with 75 to 90 percent stenosis in the LAD and 100 percent artery stenosis in the right coronary artery. Graph A shows pre-angiogram data, and graph B shows post-angioplasty data. The upslope of the bell-shaped curve begins at 50 Hz. The maximum coefficient magnitude is greater than 2.5 units at 55 Hz. The bell-shaped curve ends at 60 Hz. This technique correctly diagnosed a diseased coronary artery in this patient. Graph B shows the absence of the bell-shaped curve after the angioplasty of the LAD was performed, and stenosis similar to that of a normal patient.

Figure 8:
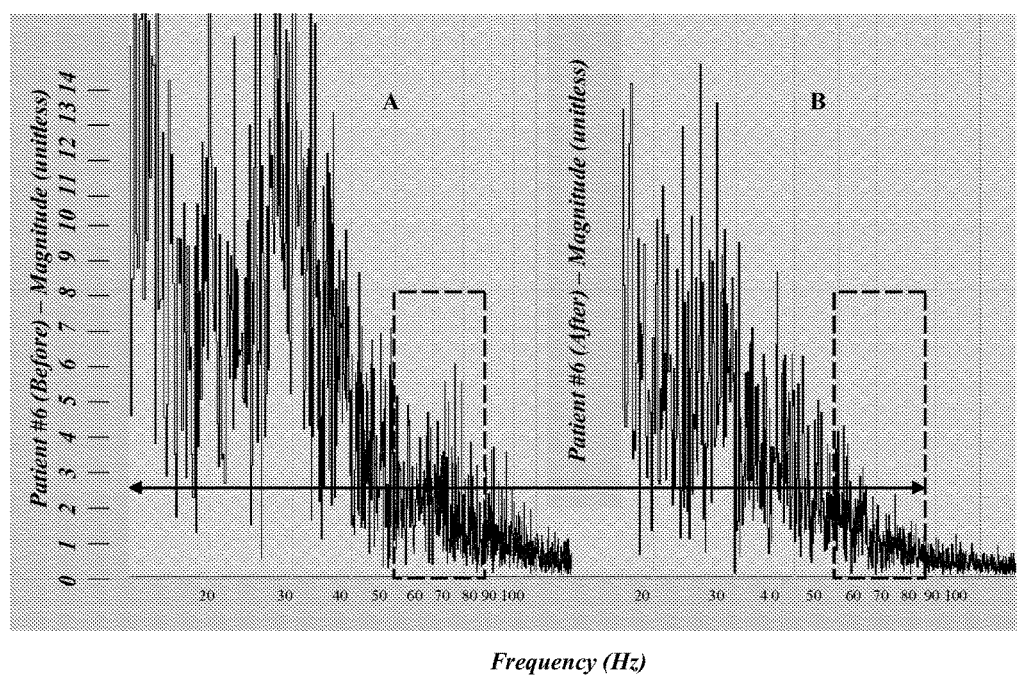
FIG. 8 shows data charts from a patient with 50-75% and 100% artery stenosis in different artery sections. Graph A shows pre-angiogram data, and graph B shows post-angioplasty data.

FIG. 8 shows data charts from a patient with 50 to 75 percent stenosis in the LAD and 100 percent artery stenosis in the right coronary artery. Graph A shows pre-angiogram data, and graph B shows post-angioplasty data. As shown, the upslope of the bell-shaped curve begins at 50 Hz, peaks above 2.5 units at 65 Hz and downslopes to end before 80 Hz. After angioplasty, graph B shows the disappearance of the bell-shaped curve due to the opening and stenting of the LAD.

Statistical analysis was then performed on the data from the fifty-one patients. If one were to consider the technique overall, it correctly detected both normal and diseased patients in 43 out of 51 cases, or 84 percent of the time.

The data was statistically analyzed by first grouping the data according to whether a patient had any stenosis in the LAD. If a patient had stenosis in other coronary arteries but not the LAD, they were considered normal. The 25-50 percent stenosed patients were included in normal because the angiogram indicated "no significant focal stenosis." There were a total of 34 normal patients. If the LAD was stenosed more than 50 percent, it was called stenosed LAD. There were a total of 17 stenosed LAD patients.

Table 1 shows how the patients were assessed in the angiogram and how well the technique performed:

TABLE 1

|  | Normal | Stenosed LAD | Total |
|---|---|---|---|
| Normal | 17 | 0 | 17 |
| Other Artery | 6 | 0 | 6 |
| 25-50% | 9 | 2 | 11 |
| Total Normal | 32 | 2 | 34 |
| 50-75% | 0 | 5 | 5 |
| 75-90% | 3 | 2 | 5 |
| 90-99% | 3 | 4 | 7 |
| Total Stenosed LAD | 6 | 11 | 17 |

All 17 normal patients were classified as normal—as were all patients with blockage in arteries other than the LAD. In the 25-50 percent stenosis category, 9 out of 11 patients were correctly called normal.

In the Stenosed LAD category, this technique correctly classified 50-99 percent blockage in 11/17 patients. Because of the low sample size within each category, patients within this classification were considered as a whole.

To break it down further, we observed a 94 percent (32/34) success in detecting normal patients. As shown in Table 1, the two patients incorrectly identified as normal were in the 25-50 percent stenosis range. This means that in our data set, the incorrectly classified patients had some stenosis in the LAD. Because we did not use intravascular ultrasound to quantify stenosis, we do not know if the patients were at the lower end (25%) or upper end (50%) of the range.

Patients with LAD (50-99 percent) stenosis were identified 11 times out of 17. This is an observed success rate of 65 percent. Thus, the results indicate the diagnosis technique has 94 percent specificity and 65 percent sensitivity.

This study was conducted to assess the feasibility of this method to detect clinically significant LAD stenosis in patients with symptoms and positive stress test where an interventional procedure was performed. In all cases, the physician who performed the intervention had no knowledge of this study and had the option of using intravascular ultrasound as needed in an individual case. We compared this technique with standard angiography, and found that this technique had a high specificity and negative predictive value for detecting coronary artery disease at the 4lics in the left anterior descending coronary artery. The high negative predictive value suggests that it may have a role in ruling in clinically significant disease in the LAD coronary artery.

With the use of this technique, 94 percent of the patients without left anterior descending coronary artery disease were identified as having no clinically significant coronary artery disease. These data support the use of this technique a method of ruling in significant disease in the left anterior descending coronary artery. Such information is clinically relevant, since predictive assessment would allow a physician to alert a patient of developing blockage and also allow more time for interventional measures to begin.

Although limited only to the left anterior descending coronary artery, this tool may be useful in screening patients with suspected coronary artery disease, atypical symptoms, family history or multiple risk factors. When the method is applied to raw acoustic information, the resulting analysis can be correlated to stenosis in the left anterior descending coronary artery.

As shown in FIGS. 4 through 8, data from several stethoscope diagnoses may be compared as the condition of a patient develops. This technique may be particularly useful in monitoring the recovery of a patient after angioplasty or placement of a stent. The blockage in an artery may return in a process called restenosis. Using a stethoscope to diagnose restenosis may allow for more frequent tests and the avoidance of multiple angiograms.

The preceding specific embodiments are illustrative of the practice of the invention. It is to be understood, therefore, that other expedients known to those skilled in the art or disclosed herein may be employed without departing from the invention or the scope of the claims.

Many embodiments of the invention have been described. Various modifications may be made without departing from the scope of the claims. These and other embodiments are within the scope of the following claims.

The invention claimed is:

1. A system for detecting coronary artery disease comprising:
   at least one vibration sensor configured to be placed over a patient's chest to obtain vibration data in a frequency range below about 100 Hz;
   a memory configured to store the vibration data from the at least one vibration sensor; and
   at least one processor configured to
      process the vibration data to obtain processed data,
      detect a bell shaped curve within the processed data,
      determine an onset frequency of the bell shaped curve,
      determine a downslope frequency of the bell shaped curve,
      determine a peak of the bell shaped curve at a peak frequency that is between the onset frequency and the downslope frequency, and
      provide an output related to a presence or absence of at least 50 percent to 99 percent coronary artery stenosis based on the onset frequency, the downslope frequency, and the peak.

2. The system of claim 1, further comprising a display coupled to the at least one processor.

3. The system of claim 2, wherein the display is configured to display the output as an indication of a presence or absence of the bell shaped curve.

4. The system of claim 3, wherein the indication comprises a graphical representation related to the processed data.

5. The system of claim 4, wherein the graphical representation comprises a plot of harmonic magnitude versus frequency.

6. The system of claim 4, wherein the graphical representation comprises an identification of the bell shaped curve if the bell shaped curve is detected.

7. The system of claim 1, further comprising a housing, wherein the at least one sensor, the memory and at least one processor are arranged in the housing.

8. The system of claim 7, further comprising a display coupled to the housing.

9. The system of claim 1, wherein the predetermined frequency range is between about 50 Hz and about 80 Hz.

10. The system of claim 1, further comprising a stethoscope comprising the at least one vibration sensor.

11. The system of claim 10, wherein the stethoscope comprises an electronic stethoscope.

12. The system of claim 1, wherein the bell shaped curve in the predetermined frequency range is indicative of about 75 percent to about 99 percent stenosis in a coronary artery.

13. The system of claim 12, wherein the coronary artery is the left anterior descending coronary artery.

* * * * *